United States Patent [19]

Naftchi

[11] Patent Number: 4,855,325

[45] Date of Patent: * Aug. 8, 1989

[54] TREATMENT OF MAMMALS SUFFERING FROM DAMAGE TO THE CENTRAL NERVOUS SYSTEM

[76] Inventor: Nosrat E. Naftchi, 389 Forest Ave., Teaneck, N.J. 07666

[ * ] Notice: The portion of the term of this patent subsequent to May 3, 2005 has been disclaimed.

[21] Appl. No.: 150,767

[22] Filed: Feb. 1, 1988

Related U.S. Application Data

[60] Division of Ser. No. 691,830, Jan. 16, 1985, Pat. No. 4,742,054, which is a continuation of Ser. No. 443,915, Nov. 23, 1982, abandoned.

[51] Int. Cl.$^4$ ................... A61K 31/155; A61K 31/55; A61K 31/495; A61K 31/52
[52] U.S. Cl. .................................. 514/634; 514/215; 514/255; 514/263; 514/385; 514/964
[58] Field of Search .............. 514/215, 225, 255, 263, 514/269, 284, 288, 401, 414, 634, 964

[56] References Cited

PUBLICATIONS

Chem. Abst. 98:192,204n, 1983; 100:168, 888c, 1984; 101:2122u, 1984.
Naftchi, Science, pp. 1042–1044, vol. 217, 1982.

*Primary Examiner*—John W. Rollins
*Attorney, Agent, or Firm*—Barry G. Magidoff

[57] ABSTRACT

A method and compositions, for treating an animal with an injured spinal cord, causing loss to sensory function and motor control, to regain such function and control. The method comprises the administration of a guanidine compound and a serotonergic receptor agonist or a dopaminergic receptor agonist, and preferably a combination with an anti-desensitization agent, such as a xanthine, a b-adrenergic receptor agonist or a vascular skeletal muscle dilator. The composition comprises a guanidine compound and a second compound acting in conjunction therewith or preventing desensitization thereof.

13 Claims, No Drawings

TREATMENT OF MAMMALS SUFFERING FROM DAMAGE TO THE CENTRAL NERVOUS SYSTEM

This is a divisional application of application Ser. No. 06/691,830, filed Jan. 16, 1985, U.S. Pat. No. 4,742,054 which is a continuation application of application Ser. No. 443,915, filed on Nov. 23, 1982, now abandoned.

This application is directed to a treatment method for mammals suffering from traumatic injury to the spinal cord, or from certain central nervous system diseases, the treatment comprising the timely administration of an $\alpha_2$-adrenergic receptor agonist. More particularly, this invention provides a method of treatment for mammals utilizing a neural receptor agonist, such as clonidine in combination with other materials which are synergistic to the activity of, e.g., clonidine, or which counteract any tendency to sub-sensitivity or tolerance of the primary treatment material. This application is further directed to a therapeutic composition useful in such treatment.

In the past, clonidine has been known to have a variety of effects. Primarily, it was known to have pronounced blood pressure-lowering properties with side effects of sedation and depression. As such, the drug had been indicated for use as a hypertension remedy. However, previously published reports have also referred to the activity of clonidine to reduce plasma renin activity, to decrease insulin secretion, and to increase the plasma level of the growth hormone in mammals. Its therapeutic uses, in addition to the treatment of hypertension, includes the treatment of migraine, glaucoma, and, very recently, as an aid in the treatment of opiate addicts to avoid severe withdrawal symptoms. In the majority of these uses, it has previously been proposed that the mechanism for the activity of clonidine is based upon its activity as an $\alpha$-adrenoceptor agonist; see, for example, *TIPS, Volume 2, No. 7, pages 194-6, July, 1981.

*Trends in Pharmacological Sciences

Previously, it has generally been assumed that traumatic injury to the spinal cord, especially one which effectively neurologically severs the cord, is, in mammals, for all practical purposes, irreversible. Some useful effect has been obtained by the treatment of an injured mammal with methyl prednisolone sodium succinate (MP) or with naloxone, to provide some relief and to prevent more extensive damage as a result of the anti-oxidant properties of these materials. In addition, and perhaps more importantly, an increase of regional blood flow and perfusion pressure is caused by naloxone (an opiate antagonist), thyrotropic releasing hormone (TRH), and $\epsilon$-aminocaproic acid ($\epsilon$-ACA). Methyl prednisolone has an anti-inflammatory effect. Unfortunately, if these drugs are not administered almost immediately, i.e., within the first hour after the initial injury, their effect is substantially nil. Further, naloxone may have a hyperalgesic effect, and the methyl prednisolone may reduce immune reaction and thus increase the possibility of infection.

It has now been discovered that by the use of a neural receptor agonist, e.g., clonidine, many of the undesirable aftereffects of traumatic spinal injury can be alleviated or completely eliminated, and, if treatment is commenced sufficiently early, at least some restoration of normal neural function with the attendant control over muscle activity, is attainable.

In accordance with this invention, a mammal having a major spinal cord injury is treated to control autonomic dysreflexia, clonus and spasticity, and to return at least partial neural function, by the administration to the injured mammal of a neural receptor agonist, including an $\alpha_2$-adrenergic, or a dopaminergic, or a serotonergic receptor agonist. The, e.g., $\alpha_2$-adrenoceptor, agonist is most preferably initially administered immediately, i.e., within one hour after the injury to the spinal cord occurs, or even prior to the injury. However, dramatic effectiveness is obtainable even when treatment is not commenced until as much as six years after the original traumatic injury occurred.

It is understood that many of the presently known $\alpha_2$-adrenergic, dopaminergic or serotonergic receptor agonists, have direct physiologic effects on the mammal being treated, usually during the early stages of treatment before tolerance develops. Such physiologic effects are often contraindicated for the mammal being treated, e.g., the hypotensive effect of clonidine. It is thus often necessary to also administer a physiologically active antagonist to counteract any such undesirable physiologic side effects. The antagonist can be administered simultaneously or sequentially, after the physiologic side effects become manifest.

When treatment commences promptly after an injury, for a better titration of the drug and control of blood pressure, the initial administration of the neural receptor agonist is preferably intravenously. An antagonist of, e.g. the $\alpha_2$-adrenergic receptor agonist, or $\alpha_2$-blocking agents, must be available to counteract any undesirable side effects of the $\alpha_2$-adrenergic receptor agonist, for example, the blood pressure decrease caused by clonidine. Such antagonists include, e.g., for clonidine, for example, phentolamine, yohimbine and tolazoline, and piperoxane. Angiotensin II, in addition to its blood pressure increasing activity, may have a synergistic effect in combination with clonidine with respect to its primary purpose of providing neural function return.

Compounds such as 5-fluorodeoxyuridine (FUDR) and 3,4 dehydroprolene may also be included as part of the therapy to prevent or reduce glial and fibroblastic scar formation, respectively. These compounds can be topically applied, for example, in combination with dimethylsulfoxide (DMSO).

It is preferred that the, e.g., $\alpha_2$-adrenergic receptor agonist, not be administered until the vital signs have stabilized after the initial spinal trauma shock. In the early stages, within the first, e.g., three hours after the initial shock, the previously known therapeutic materials such as naloxone, methyl prednisolone, dopamine or other materials, which have anti-inflammatory and blood-flow increasing effects, should also be carefully administered, together with, or immediately before or after the neural receptor agonist. In addition to their specific effects, they may also act to accelerate the effects of the primary agent. In addition, any mechanical obstruction or pressure in the region should be surgically eliminated or restructured.

Useful $\alpha_2$-adrenergic receptor agonists, include iminoimidazolines, such as tiamenidine and clonidine, and especially of the type:

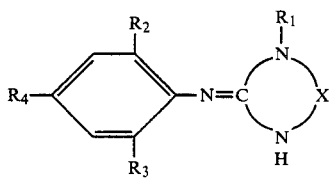

wherein

X is an alkylene group having 2-3 carbon atoms, $R_1$ is hydrogen or lower alkyl, e.g. up to 5 carbon atoms;

$R_2$, $R_3$ and $R_4$ are selected from the group consisting of methyl, ethyl, and chlorine, or their non-toxic, pharmacologically acceptable acid addition salts.

Other useful such $\alpha_2$-adrenoceptor agonists include amino-dihydrothiazines, such as xylozine; guanidines, such a guanabenz and guanfacin; and azepines, such as azepexal B-HT933 and B-HT920, having the general formula:

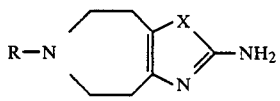

wherein R is an acyclic hydrocarbyl group of two to four carbon atoms and X is oxygen or sulfur, e.g., X=O and R is $CH_3-CH_2-$ or X=S and R is $CH_2=CH-CH_2-$.

These and other compounds which have the desired adrenergic effect, are believed to positively affect the descending neural columns. The ultimate effect is apparently to "bridge" the spinal lesion, permitting tonic, regular neural stimulation of muscles located below the spinal lesion. There is also visible some myelination around the lesion site after treatment according to this invention.

The principal active agent, the $\alpha_2$-adrenergic, for example, receptor agonist, is preferably administered with a material having an anti-desensitization effect. Although it is not as yet fully elucidated, it is believed that at least a major portion of the desensitization arises, e.g., as a result of an imbalance created in the proportion of cyclic adenosine-3',5'-monophosphate (c-AMP) present in the nervous system.

Although the mechanism is not well understood, it is believed that the anti-densensitizing agents act in combination with the principal therapeutic drug by increasing the physiologic availability of c-AMP, such as by first interfering with the catabolism of c-AMP, specifically by inhibiting the enzyme phosphodiesterase, or two, by direct action on $\beta$-receptor to increase the production of c-AMP. The effect of this is to maintain a desirable ratio of c-AMP-to-c-GMP (cyclic guanosine-3,5-monophosphate).

Such useful anti-densensitization agents include, for example, the xanthines, such as theophylline and caffeine, and $\beta$-adrenergic receptor agonists such as isoproterenol hydrochloride and metaproterenol. The use of a milder $\beta$-adrenergic agonist-vascular skeletal muscle dilator, e.g., nylidrin hydrochloride, is especially desirable after treatment has been continuing for a substantial period and minimal restoration of neural function has begun.

Furthermore, in combination with, or in place of, the $\alpha_2$-adrenergic receptor agonist, a serotonergic receptor agonist can be administered to good effect in the treatment of spinal cord damage to mammals. Useful such serotonergic receptor agonists include 5-methoxy-N,N-dimethyltryptamine(5-MDT), quipazine, 1-(N-trifluoromethylphenyl)-piperazine, 6-chloro-2-(1-piperazino) pyrazine and various indoleamines, which are known to be structurally and functionally related to serotonin. It is believed that preferably a combination of the $\alpha_2$-adrenergic receptor agonist and the serotonergic receptor agonist provide a most effective treatment agent for mammals having traumatic spinal cord injuries.

Dopaminergic receptor agonists are also effective alone or preferably combined with the $\alpha_2$-adrenoceptor agonists or serotonergic receptor agonists. Such dopaminergic receptor agonists include, for example, bromocriptine mesylate (PARLODEL ®, by Sandoz), apomorphine, piribedil, lergotrile pergolide, and a combination of levo-dopa and carbi-dopa (4:1 or 10:1 ratios, SINEMET, by Merck). The preferred dopaminergic receptor agonists are of the D2-type.[1]

[1]-ENZYMES & NEUROTRANSMITTERS IN MENTAL DISEASE, E. Usdin, et al (ed. pgs. 485-498, "Neurochemical Correlates of Amphetamine-Induced Recovery From Amnesia" by N. Eric Naftchi et al( John Wyley & Sons New York, 1980)

It has further been found that after an initially successful therapeutic regimen with a neurooogic receptor agonist, i.e., after intraspinal pathways have at least partially regained their conductivity, certain precursor compounds can also be usefully administered. For example, L-dopa, L-tryptophan or 5-hydroxytryptophan can be administered in combination with a peripheral inhibitor of L-aromatic amino acid decarboxylase (L-AADI), such as carbi-dopa, or a monoamine oxidase inhibitor (MAOI), such as depranyl. These enzyme inhibitors increase the therapeutic availability of the precursor agent to the central nervous system. The precursors are centrally converted to the natural neurotransmitters, dopamine and norepinephrine, in the case of L-dopa, and to serotonin and melatonin, in the case of L-tryptophan.

Therapeutic compounds useful for treatment in accordance with this invention are classified above by their biological activity, with specific examples given for each class, including sub-generic chemical groupings. The examples given are all known compounds which are generally commercially available, and the preparation of which can be readily obtainable from the technical literature and patents. A more complete description of each named compound can be had, chemically, from the Merck Index 9the edition, Mark Windholz, Ed. (Merck & Co. Inc., New Jersey 1976). New compounds of the same type can also be used.

Compounds useful for this invention may be used as medicaments in the form of pharmaceutical preparations which contain the desirable pharmocologically active compounds, specifically, the $\alpha_2$-adrenergic receptor agonist, and/or a dopaminergic and/or a serotenergic receptor agonist, in combination with the various secondary active ingredients defined more fully herein. These preparations are generally formed in admixture with a suitable, pharmaceutical (organic or inorganic, solid or liquid), carrier, suitable for enteral, e.g., oral, or parenteral, e.g., intravenous, administration. The suitable carriers include substances which do not undesirably react with the active compounds, such carriers include water, gelatine, lactose, starches, stearic acid, magnesium stearate, sicaryl alcohol, talc, vegetable oils, benzyl alcohols, gums, waxes, propylene glycol, polyalkylene glycols or any other know carrier for medicaments.

Solid pharmaceutical preparations which are suitable for oral administration, include capsules, tablets or dragees. Liquid formulations can include solutions, suspensions or emulsions. Auxiliary pharmaceutically inert materials which can also be present in the pharmaceutical preparations include preserving agents, stabilizing agents, wetting or emulsifying agents, and salts for varying the osmotic pressure, or buffering agents. The addition of each of these auxiliary compounds, and the use of the carriers are well known to the art and more specific instructions are not necessary for purposes of defining this invention.

Regardless of the method of administering the active compounds in accordance with this invention, e.g., the neural receptor agonist and the secondary active ingredient, it is preferred that the plasma level in the blood stream of the mammal being treated, be maintained as consistent as is feasible during the term of the treatment. It has been found that this is useful in order to reduce or substantially eliminate autonomic dysreflexia and spasticity. Failure to maintain a sufficiently constant dosage in the blood stream tends to keep the animal unprotected and create, at least, intermittent rises in blood pressure and spasticity which would interfere with treatment and ultimate recovery of the injured mammal. In order to be efficacious, we have found that, e.g., the $\alpha_2$-adrenergic receptor agonist, clonidine, should be present in the blood in a proportion of at least about 1 $\mu g/kg$ bodyweight, and preferably at least about 2 $\mu g$ to about 8 $\mu g/kg$ bodyweight, most preferably not exceeding 6 $\mu g/kg$ bodyweight.

The maximum amount of the active ingredient which can be present is generally limited by the undesirable side effects that the specific therapeutic compound may generate. For example, the hypotensive effect of clonidine, would mitigate against maintaining a high concentration of clonidine in the blood, at least during the early stages of treatment. When an animal has adapted to the drug, the concentration may be increased to levels greater even than approximately 6 $\mu g/kg$. It is thus desirable, once the animal has acquired tolerance for the active pharmacological agents of this invention, to administer the agent using a sustained release form, e.g., a sustained release capsule or a sustained release transdermal agent. When such sustained release forms are not available, the active compounds in accordance with this invention should be administered at relatively short intervals, for example, 4 to 6 times per day. Oral administration to the injured mammal is preferably based upon bodyweight.

Certain compounds, such as for example, clonidine, which are presently used as pharmaceutically active agents for other purposes, have not been formulated in sustained release form because such format is not desirable or useful in the present modes of treatment, e.g., for clonidine as a hypotensive agent. However, the preparation of sustained release forms of any compound, whether for oral administration or transdermal administration, is in fact well known.

The proportions of the secondary therapeutically active compound which can be administered to the injured mammal with the primary, e.g., $\alpha_2$-adrenergic receptor agonist, depends upon the particular activity of the individual compound, and the effect for which it is introduced. In general, it is most preferred that combined unit dosage forms of the primary and secondary therapeutic agents be administered in a single preparation; for example, capsules or tablets of the combined therapeutic agents should be formulated in the desired proportions. The xanthines, for example, are generally used, together with, e.g., an $\alpha_2$-adrenergic receptor agonist, such as clonidine, in the proportions by weight of at least about 500 parts xanthine: 1 part $\alpha_2$-adrenergic receptor agonist, and preferably in a proportion of not greater than about 2000:1, respectively. For example, the combination of theophylline and an $\alpha_2$-adrenergic receptor such as clonidine, is preferably formulated in the ratio of about 1000:1 to about 1500:1, by weight. Those compounds which are combined primarily to offset an undesirable side effect of the primary therapeutic agent, must be administered in a unit dosage form sufficient to provide such blocking or antagonism, without interfering with the primary therapeutic effect of the primary agent.

The procedures and products of this invention are illustrated by the following examples. These examples are merely for the purposes of exemplifying the invention, and for clarifying a specific means of treatment, without being exclusive of the full scope of this invention.

COMPARATIVE EXAMPLE 1

A cat was anesthetized using intravenous pentobarbital (30 mg/kg) after which its arterial blood pressure was continuously monitored for at least two hours. After recording the stable initial arterial blood pressure, a dorsal laminectomy was performed in the thoracic region of the cat from $T_3$ to $T_5$. After restoration of blood pressure, the cat was then traumatized by means of a twenty gram weight being dropped from a height of twenty-five centimeters (500 g-cm force) on the exposed spinal column dura at the fourth thoracic segment.

The cat was not thereafter treated except to surgically clean the trauma region and assist in the healing of the surgery.

The cat was regularly observed over a four-month period.

Somatosensory-evoked potentials (SEPs) were measured and recorded for this cat, immediately before the trauma, 10 minutes after the trauma and 20 minutes after the trauma and then again 30 days after impact of the 500 gram centimeter force. The SEPs were generated by stimulating the sciatic nerve by means of needle electrodes inserted through the posterior thighs. It is known that the recording of SEPs from the lower extremities requires the presence of intact ascending pathways. The absense of SEPs indicates a complete disruption of the spinal cord tracks. Beginning 10 minutes after impact, the SEP was substantially completely absent from the thus injured cat.

The cat did not regain the use of its lower extremities, nor did it ever regain bladder and bowel control. The animal progressed from acute, flaccid phase to the chronic, spastic and autonomically dysreflexic phase of paralysis.

EXAMPLES 1-7

A group of seven (7) cats of approximately equal size were traumatically injured in accordance with the procedures set forth in the Comparative Example above.

After surgical cleaning and mechanical treatment of the wound, in an identical fashion to that carried out in the Comparative Example, intravenous infusion of a clonidine solution (5 micrograms/ml in 15 ml of saline solution) was commenced. The intravenous solution was infused twice per day, 15 ml of the solution at each administration. Immediately after infusion of the clonidine, Angiotensin II (0.1 mg. per kg of bodyweight) was slowly infused to bring the arterial blood pressure up to the initial stabilized level; a total of 0.075 mg of clonidine and 0.1 mg/kg of Antiotensin II were given to each cat that first day.

On the second day of treatment, the clonidine was orally administered twice a day, each administration being a 0.1 mg tablet of clonidine. On day three, the oral treatment was repeated. On day four of the treatment, the cats received a 0.1 mg clonidine tablet in the morning and intravenous infusions of clonidine and Angiotensin II in the same total amounts as on the first day of treatment. Upon continuing recording of the SEPs, a measurable SEP was found to have returned on the fourth day of treatment. Beginning on day five of treatment, each cat received 0.05 mg clonidine tablet four times daily.

On the fifth day of treatment, the cat was able to move its tail and responded to pinching of the hind quarters by withdrawal of the hind legs. while the oral administration of clonidine tablets continued as described above, the cat started to walk, in a controlled manner, and upon testing, all tactile, thermal pressure and pain sensations, as well as motor coordination, seemed to have returned. The recorded SEPs indicated normal activity.

Continued testing of six other cats in accordance with the above procedure, wherein the clonidine treatment commenced between 14 and 48 days after the impact, was carried out. Once treatment began, however, the same treatment regimen as described above was continued for all of the cats. All six cats which received initial clonidine treatments not more than 48 days after the traumatically induced paralysis occurred, regained the ability to walk.

EXAMPLE 8

A sixty kilogram mammal suffering from a traumatic spinal column injury, resulting in a serious lesion or severance of the spinal cord, is initially surgically treated to remove compression on the spinal cord and a blockade of the flow of cerebrospinal fluid.

Even before such surgery is started, and preferably within 1 or 2 hours after the initial injury, the sixty kg mammal is treated with a single dose of methylprednisolone sodium succinate (35 mg/kg), by intravenous infusion. Naloxone or dopamine can be used in its place.

Promptly after the surgery was completed, the animal is started on an oral dosage of clonidine, 0.025 mg q.i.d. and then an oral dose of bromocriptine mesylate 1.25 mg. b.i.d. The animal is continuously monitored for blood pressure changes. As soon as the animal's blood pressure has stabilized (within two days), the oral dose was raised to 0.05 q.i.d. of clonidine. If an excessive drop in the blood pressure of the sixty kg mammal occurred, a suitable hypertensive agent is administered, such as the octapeptide, Angiotensin II, or alternatively an α-adrenergic antagonist, such as phentolamine and tolazoline. Generally, the blood pressure should not be permitted to drop below 85/60 in the rest position.

After the clonidine has been administered for four weeks, the animal is found to have a reduced sensitivity to the therapeutic effectiveness of the clonidine, so that oral administration of sustained release theophylline tablets (200–250 mg b.i.d.) was commenced.

The injured mammal is continually monitored to record the somatosensory-evoked potential derived by the electrode stimulation of the sciatic nerve.

Six months after clonidine treatment is commenced, the recorded SEP indicates that intraspinal and spinal reflex pathways commenced conducting. Thereafter, a suitable dopaminergic receptor agonist, such as bromocriptine, can be added to the treatment at regular intervals. In addition, the levels of desirable neurally active compounds can be increased by the administration of a dopaminergic receptor agonist precursor optimally, plus a serotonergic receptor agonist precursor, in combination with a peripheral inhibitor, L-AADI, alone or with an MAOI, e.g., depranyl. A useful combined such additional pharmocological composition comprises L-dopa(100 mg), L-tryptophan (250 mg), and carbidopa (25 mg), administered at least twice per day, two days each week. Administration of additional therapeutic agents can be started generally from one to six weeks after receptor agonist treatment has commenced, depending upon how soon after the onset of injury treatment begins.

EXAMPLE 9

The spinal cord of a small mammal (300–350 g) was completely transected surgically with sharp scissors. Before surgery, the animal received 0.1 mg per kg clonidine intraperitoneally (i.p.) together with anesthesia. Thereafter, the animal was given the same dose b.i.d., twice each day. After fourteen (14) days of this therapy, the animal could walk with coordinated alternate movements of the hind limbs. The control animal, which received no post-operative treatment, dragged its hind limbs and went into reflexed stepping (not coordinated walking) ninety days after transection.

It is desirable to maintain a substantially constant level of the receptor agonist, such as clonidine, and a $D_2$-dopaminergic receptor agonist, such as bromocriptine, in the blood plasma. It is for this reason, that the oral administration of the clonidine, when not done using a sustained release agent, should be as often as once every four hours. Failure to maintain a constant plasma level has been found to result in an undesirable return in spasticity. Bromocriptine has a synergistic effect in combination with clonidine on relieving spasticity.

Therefore, preferably, an oral or transdermal administration is accomplished using the sustained release or time-delayed dosage forms. The therapeutically active agents ca be combined into such forms in a known manner.

When using a combination of pharmacologically active agents, it is preferred that a single administering medium should contain the desired proportions of, for example, the $\alpha_2$-adrenergic receptor agonist and a $D_2$-dopaminergic receptor agonist, plus any other secondary active agent. For example, such a useful sustained release capsule would contain 0.15 mg clonidine and 1.25 mg bromocriptine. As it is desirable in the extended treatment of a sixty kg mammal to gradually increase the thus administered agent, other sustained release forms should be obtained having the following proportions of active ingredients, for example:

0.15 mg clonidine and 1.25 mg bromocriptine mesylate
0.2 mg clonidine and 2.5 mg bromocriptine mesylate
0.3 mg clonidine and 2.5 mg bromocriptine mesylate 0.4 mg clonidine and 2.5 mg bromocriptine mesylate
0.5 mg clonidine and 3.5 mg bromocriptine mesylate
0.6 mg clonidine and 4.0 mg bromocriptine mesylate
0.9 mg clonidine and 6.0 mg bromocriptine mesylate
0.15 mg clonidine and 6.0 mg bromocriptine mesylate
0.9 mg clonidine and 1.25 mg bromocriptine mesylate Such administered unit dosage forms can also include from 100 to 250 mg of a material, e.g. as theophylline; similar combinations can be prepared for transdermal use. At least 200 mg of theophylline is preferred if the mammal is able to tolerate that material in its digestive system. The latter problem is avoided in transdermal administration.

Where the injured mammal is initially unconscious, it is, of course, generally advisable to make the first administration intravenously, generally in either a saline or glucose solution. The $\alpha_2$-adrenergic, dopaminergic or serotonergic receptor agonist should be administered slowly over a one hour period, each period commencing at six-hour intervals, i.e., four administrations per day.

The preferred method of continuing administration of the active pharmacologic agents of this invention is transdermally or by oral ingestion of a sustained release form of medicament. The production of such sustained release forms is well known and need not constitute any part of this invention. For example, a common form of sustained release tablet is formed by admixing the pharmacologically active ingredients with a composition comprising a higher aliphatic alcohol, such as an 8-to-18 carbon atoms alkanol, with a selectively hydrated hydroxyalkyl cellulose compound.

It is of course possible to package the active pharmacologic agents of this invention into a capsule, or the like, wherein different portions of the active agents can be released at different, predetermined times.

Finally, it has been found that the primary therapeutic agents of this invention, including the $\alpha_2$-adrenergic receptor agonist and the serotonergic receptor agonist and the dopaminergic receptor agonist, can provide a certain degree of precautionary protection against subsequent injury, i.e., almost a prophylactic effect. It has been found that the administration of a dosage of the primary therapeutic agent, prior to the receiving of a traumatic injury, further increases the chances of ultimately recovering substantially complete function of the lower limbs, and also decreasing the time before such complete recovery is attained. Such precautionary administration could usefully be carried out before placing the mammal in a potentially dangerous situation.

It is also known that a problem affecting such traumatically injured mammals with spinal cord lesions is the loss of the normal ability had by warm-blooded animals to maintain a proper body temperature over a relatively wide range of ambient temperatures. There is apparently a loss of control and receptivity between the thermal receptors below the lesion and the hypothalamus. Mammals treated according to this invention regain this ability, including the ability to perspire below the lesion.

The patentable embodiments which are claimed are as follows:

1. A pharmacologically active composition useful for treating a mammal having an injured spinal cord with a resultant loss of motor and sensory function, to restore at least partially the lost sensory-motor functions, the composition comprising a unit dosage amount of a neural receptor agonist which is a guanidine compound, as a primary therapeutic agent, and an anti-desensitization agent.

2. The composition of claim 1 wherein the antidesensitization agent is selected from the group consisting of xanthines, B-adrenergic receptor agonists and vascular-skeletal muscle dilators.

3. A pharmacologically active composition useful for treating a mammal having an injured spinal cord with a resultant loss of motor and sensory function, to restore at least partially the lost sensory-motor functions, the composition comprising a unit dosage amount of a guanidine compound and at least one other type of pharmacologically active neural receptor agonist selected from the group of types consisting of $D_2$-dopaminergic receptor agonists and serotonergic receptor agonists.

4. A pharmacologically active composition useful for treating a mammal having an injured spinal cord with a resultant loss of motor and sensory function, to restore at least partially the lost sensory-motor functions, the composition comprising a unit dosage amount of a neural receptor agonist which is a guanidine compound, the guanidine compound having undesirable physiologic side effects, and a unit dosage amount of an antagonist to overcome such side effects.

5. The composition of claim 4 comprising guanabenz and a hypertensive agent.

6. The composition of claim 5 wherein the hypertensive agent is angiotensin II.

7. A method for treating a mammal having an injured spinal cord with the resultant loss of motor and sensory function and the concomitant loss of muscular control, comprising administering to the mammal at least one neural receptor agonist which is a guanidine compound, as the primary therapeutic agent, in dosage amount and at a dosage rate sufficient to at least partially restore the lost motor and sensory function as evidenced by a return of motor and sensory functions.

8. The method of claim 7 comprising in addition administering an anti-desensitization agent in a unit dosage amount sufficient to maintain the active effect of the primary therapeutic agent.

9. The method of claim 8 wherein the anti-desensitization agent is selected from the group consisting of xanthines, $\beta$-adrenergic receptor agonists and vascular-skeletal muscle dilators.

10. The method of claim 9 wherein the primary active agent is guanobenz and the anti-desensitization agent is theophylline.

11. The method of claim 7 comprising in addition administering at least one other primary therapeutic agent selected from the group of types consisting of serotonergic receptor agonists, and and $D_2$dopaminergic receptor agonists, in combination with the guanidine compound.

12. The method of claim 7 further comprising the administration of an antagonist to counteract any undesirable physiologic side effect of the primary therapeutic agent.

13. The method of claim 12 wherein the primary agent is guanabenz and the antagonist is a hypertensive agent.

* * * * *